(12) United States Patent
Dean et al.

(10) Patent No.: US 7,205,129 B1
(45) Date of Patent: Apr. 17, 2007

(54) METHOD FOR REDUCING ARTIFACTS IN NUCLEIC ACID AMPLIFICATION

(75) Inventors: Frank B. Dean, Guilford, CT (US); A. Fawad Faruqi, Guilford, CT (US)

(73) Assignee: Qiagen GmbH, Hilden (DE)

( * ) Notice: Subject to any disclaimer, the term of this patent is extended or adjusted under 35 U.S.C. 154(b) by 0 days.

(21) Appl. No.: 09/514,113

(22) Filed: Feb. 28, 2000

(51) Int. Cl.
*C12P 19/34* (2006.01)
*C12Q 1/68* (2006.01)
*C07H 21/04* (2006.01)

(52) U.S. Cl. .................. 435/91.2; 435/6; 435/183; 536/23.1; 536/24.33

(58) Field of Classification Search .............. 435/6, 435/91.1, 91.2; 536/23.1, 24.3, 24.33, 25.3
See application file for complete search history.

(56) References Cited

U.S. PATENT DOCUMENTS

| | | | |
|---|---|---|---|
| 5,487,993 A * | 1/1996 | Herrnstadt et al. | 435/488 |
| 5,512,438 A * | 4/1996 | Ecker | 435/6 |
| 5,573,907 A | 11/1996 | Carrino et al. | |
| 5,656,461 A * | 8/1997 | Demers | 435/91.1 |
| 5,792,607 A | 8/1998 | Backman et al. | |
| 5,849,544 A * | 12/1998 | Harris et al. | 435/91.2 |
| 5,854,033 A | 12/1998 | Lizardi | |
| 5,866,336 A | 2/1999 | Nazarenko et al. | |
| 5,876,924 A | 3/1999 | Zhang et al. | |
| 5,942,391 A | 8/1999 | Zhang et al. | |
| 6,001,611 A | 12/1999 | Will | |
| 6,027,923 A * | 2/2000 | Wallace | 435/91.2 |

(Continued)

FOREIGN PATENT DOCUMENTS

EP 0 745 690 A2 12/1996
EP 0866071 A2 9/1998
WO WO 97/16566 A1 5/1997

(Continued)

OTHER PUBLICATIONS

Sommers and Tautz, "Minimal homology requirements for PCR primrs," Nucleic Acids Research, 1989, vol. 17, No. 16, p. 6749.*
Sommer and Tautz, "Minimal homology requirements for PCR primers," Nucleic Acids Research, vol. 17, No. 16, 1989, p. 6749.*
Asseline, et al., "Solid-phase preparation on 5', 3'-Heterobifunctional oligonucleotides using modified solid supports," Tetrahedron 48:1233-1254 (1992).

(Continued)

*Primary Examiner*—Bradley L. Sisson
(74) *Attorney, Agent, or Firm*—Needle & Rosenberg, P.C.

(57) ABSTRACT

Disclosed are compositions and methods useful for reducing the formation of artifacts during nucleic acid amplification reactions. The method uses special oligonucleotides, referred to herein as template-deficient oligonucleotides, that cannot serve as a template for nucleic acid synthesis over part of their length. This prevents the oligonucleotides from serving as effective templates in the formation of artifacts. The disclosed method involves using a template-deficient oligonucleotide as at least one of the oligonucleotides (preferably a primer) in a nucleic acid amplification reaction, where the template-deficient oligonucleotide comprises one or more template-deficient nucleotides, preferably at or near the 5' end of the template-deficient oligonucleotide. The disclosed method is useful for reducing artifacts in any nucleic acid amplification reaction involving oligonucleotides. In a preferred form of the method the nucleic acid amplification reaction does not involve thermal cycling. The disclosed method is effective at reducing non-cycle oligonucleotide-based artifacts. Also disclosed are kits useful for reducing artifacts in nucleic acid amplification reactions. The disclosed kits include a template-deficient oligonucleotide, wherein the template-deficient oligonucleotide comprises one or more template-deficient nucleotides, and a nucleic acid polymerase.

25 Claims, 5 Drawing Sheets

U.S. PATENT DOCUMENTS

| | | | |
|---|---|---|---|
| 6,033,881 | A | 3/2000 | Himmler et al. |
| 6,096,880 | A | 8/2000 | Kool et al. |
| 6,117,635 | A | 9/2000 | Nazarenko et al. |
| 6,124,120 | A | 9/2000 | Lizardi |
| 6,140,055 | A * | 10/2000 | Todd et al. ............... 435/6 |
| 6,143,495 | A | 11/2000 | Lizardi et al. |
| 6,183,960 | B1 | 2/2001 | Lizardi |
| 6,210,884 | B1 | 4/2001 | Lizardi |
| 6,221,603 | B1 | 4/2001 | Mahtani et al. |
| 6,255,082 | B1 | 7/2001 | Lizardi et al. |
| 6,265,559 | B1 * | 7/2001 | Gildea et al. ............ 536/23.1 |
| 6,280,949 | B1 | 8/2001 | Lizardi |
| 6,291,187 | B1 | 9/2001 | Kingsmore et al. |
| 6,316,230 | B1 * | 11/2001 | Egholm et al. ............ 435/91.1 |
| 6,323,009 | B1 | 11/2001 | Lasken et al. |
| 6,329,150 | B1 | 12/2001 | Lizardi et al. |
| 6,344,329 | B1 | 2/2002 | Lizardi |
| 6,361,940 | B1 * | 3/2002 | Van Ness et al. ............ 435/6 |

FOREIGN PATENT DOCUMENTS

| | | |
|---|---|---|
| WO | WO 97/19193 | 5/1997 |
| WO | WO 97/19193 A2 | 5/1997 |
| WO | WO 98/14610 | 4/1998 |
| WO | WO 99/18241 A1 | 4/1999 |
| WO | WO 99/31276 | 6/1999 |
| WO | WO 00/71562 A1 | 11/2000 |

OTHER PUBLICATIONS

Banér, et al., "Signal amplification of padlock probes by rolling circle replication," *Nucleic Acids Res.* 26(22):5073-8 (1998).

Beigelman, et al., "Synthesis of 1-Deoxy-D-Ribofuranase phosphoramidite and the incorporation of abasic nucleotides in stem-loop II of a hammerhead ribozyme," *Bioorganic & Medicinal Chemistry Letters* 4(14):1715-1720 (1994).

Birkenmeyer & Mushahwar, "DNA probe amplification methods," *J. Virological Methods* 35:117-126 (1991).

Bloch, et al., "Alpha-anomeric DNA: beta-RNA hyrids as new synthetic inhibitors of *Eschericha coli* RNase H, *Drosophila* embryo RNase H and M-MLV reverse transcriptase," *Gene* 72(1-2):349-60 (1988).

Brownie, et al., "The elimination of primer-dimer accumulation in PCR," *Nucleic Acids Res.* 25(16):3235-41 (1997).

Cocuzza, "A phosphoramidite reagent for automated solid phase synthesis of 5'-biotinylated oligonucleotides," *Tetrahedron Lett.* 30:6287-6290 (1989).

Compton, "Nucleic acid sequence-based amplification," *Nature.* 350(6313):91-2 (1991).

Connolly & Rider, "Chemical synthesis of oligonucleotides containing a free sulphydryl group and subsequent attachment of thiol specific probes," *Nucleic Acids Res.* 13(12):4485-502 (1985).

Connolly, "The synthesis of oligonucleotides containing a primary amino group at the 5'-terminus," Nucleic Acids Res. 15(7):3131-9 (1987).

Craxton, et al., "Linear amplification sequencing, a powerful method for sequencing DNA," *Methods: A Companion in Methods in Enzymology* 3:20-26 (1991).

Dolinnaya, et al., "Oligonucleotide circularization by template-directed chemical ligation," *Nucleic Acids Res.* 21(23):5403-7 (1993).

Dreyer & Dervan, "Sequence-specific cleavage of single-stranded DNA: oligodeoxynucleotide-EDTA X Fe(II)," *Proc. Acad. Sci. U. S. A.* 82(4):968-72 (1985).

Durand, et al., "Circular dichroism studies of an oligodeoxyribonucleotide containing a hairpin loop made of a hexaethylene glycol chain: conformation and stability," *Nucleic Acids Res.* 18(21):6353-9 (1990).

Egholm, et al., "Peptides Nucleic Acids (PNA). Oligonucleotide Analogues with an Achiral Peptide Backbone," *J. Am. Chem. Soc.* 114:1895-1897 (1992).

Ferrie, et al., "Development, multiplexing, and application of ARMS tests for common mutations in the CFTR gene," *Am. J. Hum. Genet.* 51(2):251-62 (1992).

Grzybowski, et al., "Synthesis and antibody-mediated detection of oligonucleotides containing multiple 2,4-dinitrophenyl reporter groups," *Nucleic Acids Res.* 21(8):1705-12 (1993).

Gupta, et al., "A universal solid support for the synthesis of 3'-thiol group containing oligonucleotides," *Tetrahedron Lett.* 31:2471-2474 (1990).

Huryn & Okabe, "AIDS-driven nucleoside chemistry," *Chem. Rev.* 92:1745-1768 (1992).

Jablonski, et al., "Preparation of oligodeoxynucleotide-alkaline phosphatase conjugates and their use as hybridization probes," *Nucleic Acids Res.* p, 14(15):6115-28 (1986).

Jones, et al., "Studies on the alkylation of 2', 3-40 -o-isopropylideneuridine," *J. Carbohydrates Nucleosides, Nucleotides* 4:301-6 (1977).

Jun-Dong & Li-He, "Application of Wittig reaction to adenosine derivatives," *Synthesis* 909-911 (1990).

Kalnik, et al., "NMR studies of abasic sites in DNA duplexes: Deoxyadenosine stacks into the helix opposite the cyclic analogue of 2-Deoxyribose," *Biochemistry* 27:924-931 (1998).

Kumar, et al., "A simple method for introducing a thiol group at the 5'-end of synthetic oligonucleotides," *Nucleic Acids Res.* 19(16):4561 (1991).

Landegren, "Molecular mechanics of nucleic acid sequence amplification," *Trends Genet.* 9(6):199-204 (1993).

Landegren, et al., "A ligase-mediated gene detection technique," *Science* 241:1077-1080 (1988).

Li, et al., "Enzyme-linked synthetic oligonucleotide probes: non-radioactive detection of enterotoxigenic *Escherichia coli* in faecal specimens," *Nucleic Acids Res.* 15(13):5275-87 (1987).

Lizardi, et al., "Mutation detection and single-molecule counting using isothermal rolling-circle amplification," *Nat. Genet.* 19(3):225-32 (1998).

Mackellar, et al., "Synthesis and physical properties of anti-HIV antisense oligonucleotides bearing terminal lipophilic groups," *Nucleic Acids Res.* 20(13):3411-7 (1992).

Matray & Kool, "A specific partner for abasic damage in DNA," *Nature* 399(6737):704-8 (1999).

Moran, et al., "Non-hydrogen bonding 'terminator' nucleosides increase the 3'- end homogeneity of enzymatic RNA and DNA synthesis," *Nucleic Acids Res.* 24(11):2044-52 (1996).

Nelson, "Rapid detection of genetic mutations using the chemiluminescent hybridization protection assay (HPA): overview and comparison with other methods," *Crit. Rev. Clin. Lab. Sci.* 35(5):369-414 (1998).

Nelson, et al., "Oligonucleotide labeling methods. 3. Direct labeling of oligonucleotides employing a novel, non-nucleosidic, 2-aminobutyl-1,3-propanediol backbone," *Nucleic Acids Res.* 20(23):6253-9 (1992).

Nielsen, et al., "Sequence-selective recognition of DNA by strand displacement with a thymine-substituted polyamide," *Science* 254(5037):1497-500 (1991).

Pieles & Englisch, "Psoralen covalently linked to oligodeoxyribonucleotides: synthesis, sequence specific recognition of DNA and photo-cross linking to pyrimidina residues of DNA," *Nucleic Acids Res.* 17(1):285-99 (1989).

Pieles, et al., "Preparation of a novel psoralen containing deoxyadenosine building block for the facile solid phase synthesis of psoralen-modified oligonucleotides for a sequence specific crosslink to a given target sequence," *Nucleic Acids Res.* 17:8967-78 (1989).

Ray & Jaxa-Chamiec, "Novel thymidine analogues via reaction of unprotected 5'-Deoxy-5'-iodothymidine with dianions," *Heterocycles* 31(10):1777-1780 (1990).

Robins & Wouk, "Fluorination at C5' of nucleosides, synthesis of the new class of 5'-Fluoro-5'-S-Aryl (Alkyl) thionucleosides from adenosine," *Tetrahedron Lett.* 29:5729-32 (1988).

Salunkhe, et al., "Control of folding and binding of oligonucleotides by use of a nonnucleotide linker," *J. Amer. Chem. Soc.* 114:8768-8772 (1992)

Séquin, "Nucleosides and nucleotides, Part 7. Four dithymidine monophosphates with different anomeric configurations, their synthesis and behaviour towards phosphodiesterases," *Helv. Chim. Acta.* 57(1):68-81 (1974).

Sinha & Cook, "The preparation and application of functionalised synthetic oligonucleotides: III. Use of H-phosphonate derivatives of protected amino-hexanol and mercapto-propanol or -hexanol," *Nucleic Acids Res.* 16(6):2659-69 (1988).

Sproat, et al., "The synthesis of protected 5'-mercapto-2-40, 5'-dideoxyribonucleoside-3'-O-phosphoramidites; uses of 5'-mercapto-oligodeoxyribonucleotides," *Nucleic Acids Res.* 15(12):4837-48 (1987).

Stein, et al., "Mode of action of 5'-linked cholesteryl phosphorothioate oligodeoxynucleotides in inhibiting syncytia formation and infection by HIV-1 and HIV-2 in vitro," *Biochemistry* 30(9):2439-44 (1991).

Stump, et al., "The use of modified primers to eliminate cycle sequencing artifacts," *Nucleic Acids Res.* 27(23):4642-8 (1999).

Takasugi, et al., "Sequence-specific photo-induced cross-linking of the two strands of double-helical DNA by a psoralen covalently linked to a triple helix-forming oligonucleotide," *Proc. Natl. Acad. Sci. U. S. A.* 88(13):5602-6 (1991).

Takeshita, et al., "Oligodeoxynucleotides containing synthetic abasic sites. Model substrates for DNA polymerases and apurinic/apyrimidinic endonucleases," *J. Biol. Chem.* 262(21):10171-9 (1987).

Tanaka, et al. "Cleavage of a nucleosidic oxetane with carbanions: synthesis of a highly promising candidate for anti-HIV agents: A phosphokate isosters O AZI' 5'-phosphate," *Tetrahedron Lett.* 30:2567-2570 (1989).

Thomas, et al., "Amplification of padlock probes for DNA diagnostics by cascade rolling circle amplification or the polymerase chain reaction," *Arch. Pathol. Lab. Med.* 123(12):1170-6 (1999).

Thoung & Chassignol, "Solid phase synthesis of oligo- and oligodeoxynucleotides," *Tetrahedron Lett.* 29:5905-8 (1988).

Walker, et al., "Strand displacement amplification—an isothermal, in vitro DNA amplification technique," *Nucleic Acids Res.* 20(7):1691-6 (1992).

Walker, et al., "Isothermal in vitro amplification of DNA by a restriction enzyme/DNA polymerase system," *Proc. Natl. Acad. Sci. U. S. A.* 89(1):392-6 (1992).

Will, et al., "The synthesis of oligonucleotides that contain 2,4-dinitrophenyl reporter groups," *Carbohydr. Res.* 216:315-22 (1991).

Zhang, et al., "Amplification of target-specific, ligation-dependent circular probe," *Gene* 211(2):277-85 (1998).

Zuckermann, et al., "Efficient methods for attachment of thiol specific probes to the 3'-ends of synthetic oligodeoxyribonucleotides," *Nucleic Acids Res.* 15(13):5305-21 (1987).

Baner et al. Signal Amplification of Padlock Probes by Rolling Circle Replication, *Nucleic Acids Research*, Oxford, Oxford University Press, Surrey, 26(22):5073-5078 (1998), XP002112357.

Gusev et al. Rolling Circle Amplification: A New Approach to Increase Sensitivity for Immunohistochemistry and Flow Cytometry, *American Journal of Pathology*, 159(1): 63-69 (Jul. 2001).

Lizardi et al. Mutation Detection and Single-Molecule Counting Using Isothermal Rolling-Circle Amplification, *Nature Genetics*, 19:225-232 (1988)

Mullenix et al. Allergen-specific IgE Detection on Microarrays Using Rolling Circle Amplification: Correlation with in Vitro Assays for Serum IgE, *Clinical Chemistry*, 47(10):1926-1929 (2001).

Nuovo, et al. In Situ Amplification Using Universal Energy Transfer-labeled Primers, *The Journal of Histochemistry & Cytochemistry, The Histochemical Society*, Inc., New York, New York 43(3):273-279 (1999), XP008002684.

Schweitzer et al. Immunoassays with Rolling Circle DNA Amplification: A Versatile Platform for Ultrasensitive Antigen Detection, *PNAS*, 97(18):10113-10119 (Aug. 29, 2000).

Schweitzer et al. Multiplexed Protein Profiling on Microarrays by Rolling-Circle Amplification, *Nature Biotechnology*, 20:359-365 (Apr. 2002).

Tyagia et al. Molecular Beacons: Probes that Fluoresce upon Hybridization, *Nature Biotechnology*, 14:303-308 (Mar. 1996), XP000196024.

* cited by examiner

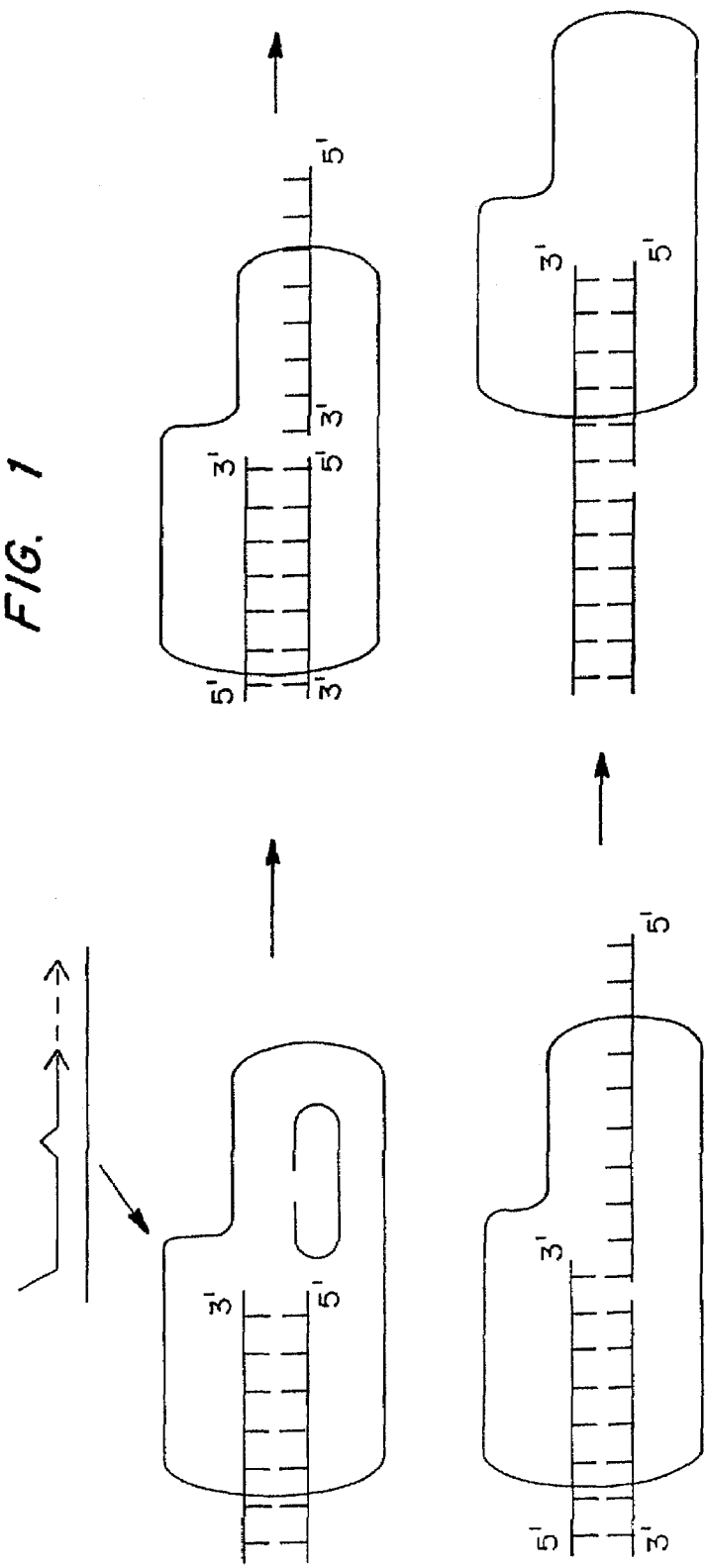
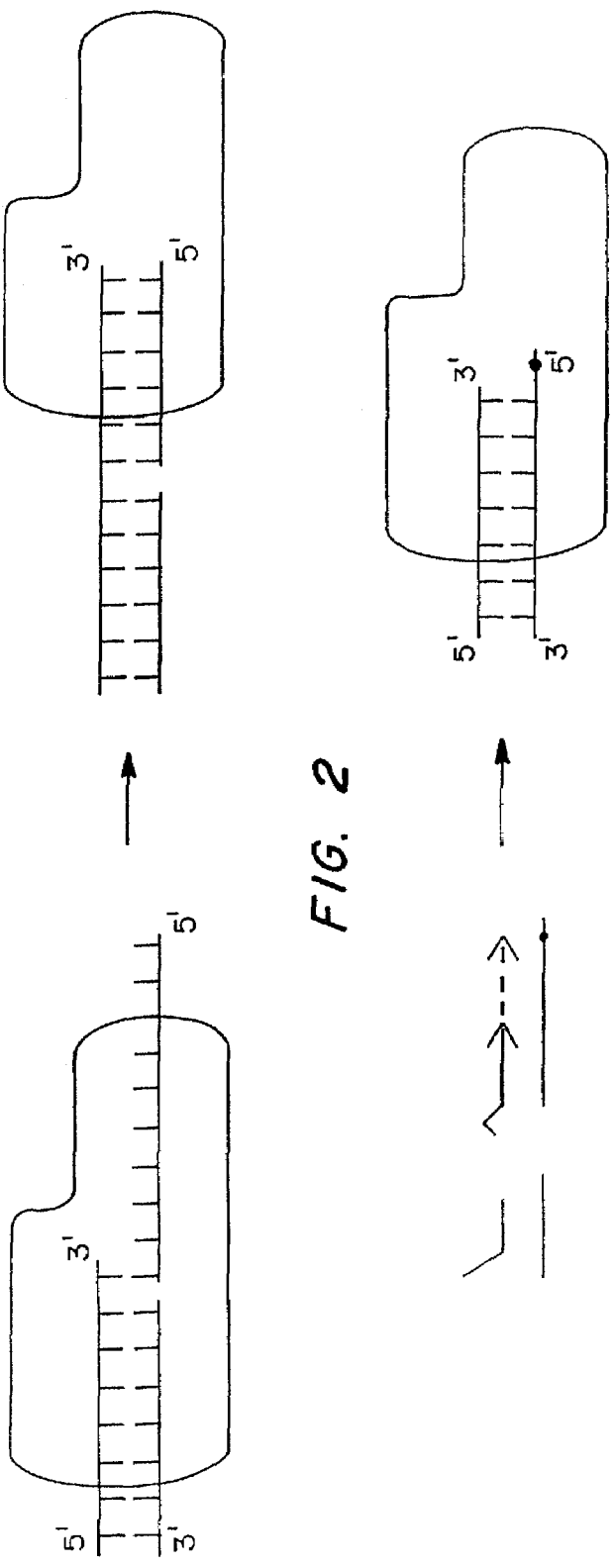
FIG. 1
FIG. 2

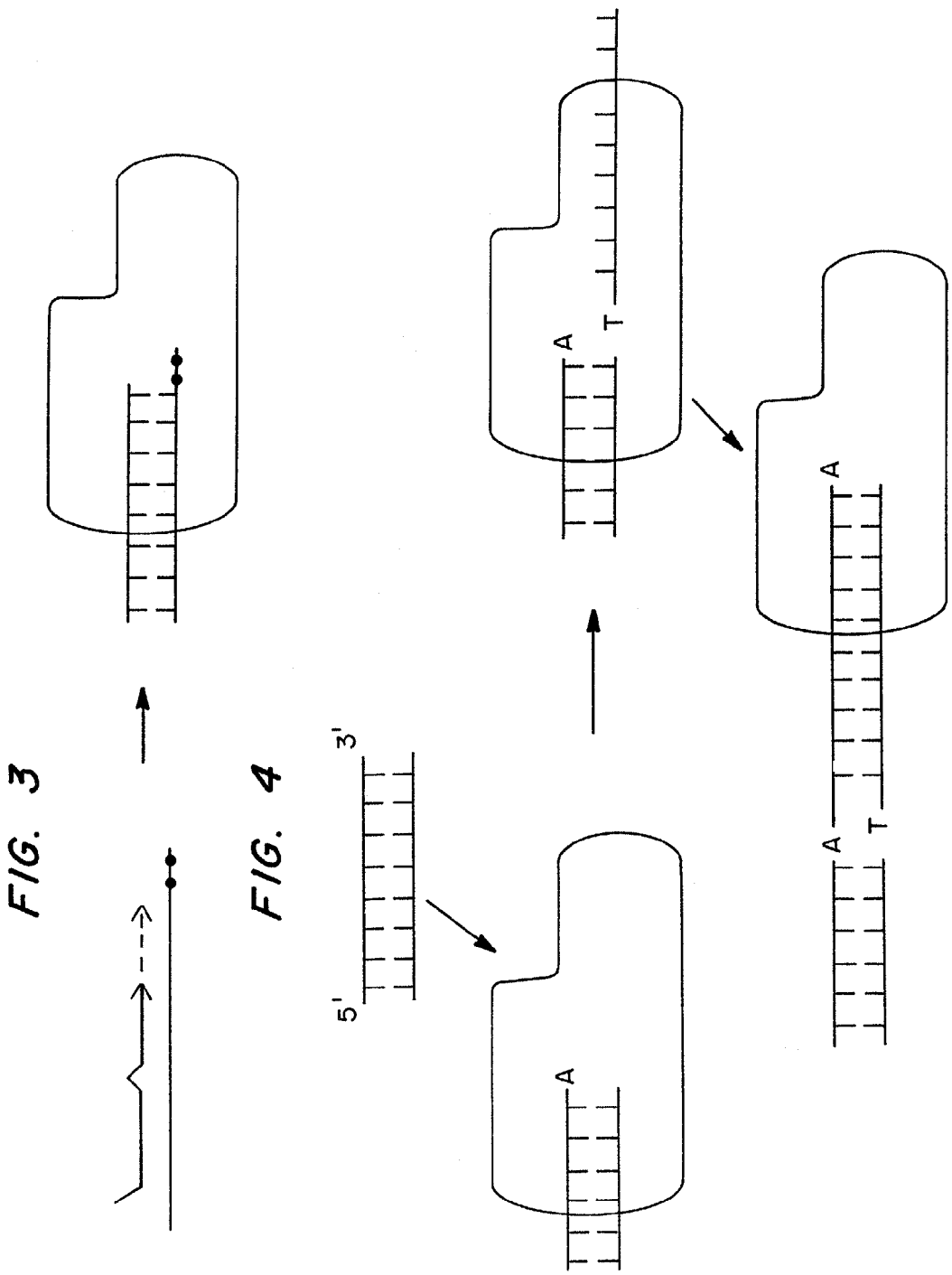

LEGEND

▞▞▞▞▞  TEMPLATE-DEFICIENT & PRIMER-DEFICIENT NUCLEOTIDES

\\\\\\\  TEMPLATE-DEFICIENT & PRIMER-CAPABLE NUCLEOTIDES

HHHHHHHH  TEMPLATE-CAPABLE & PRIMER-DEFICIENT NUCLEOTIDES

=-=-=-=  TEMPLATE-CAPABLE & PRIMER-CAPABLE NUCLEOTIDES

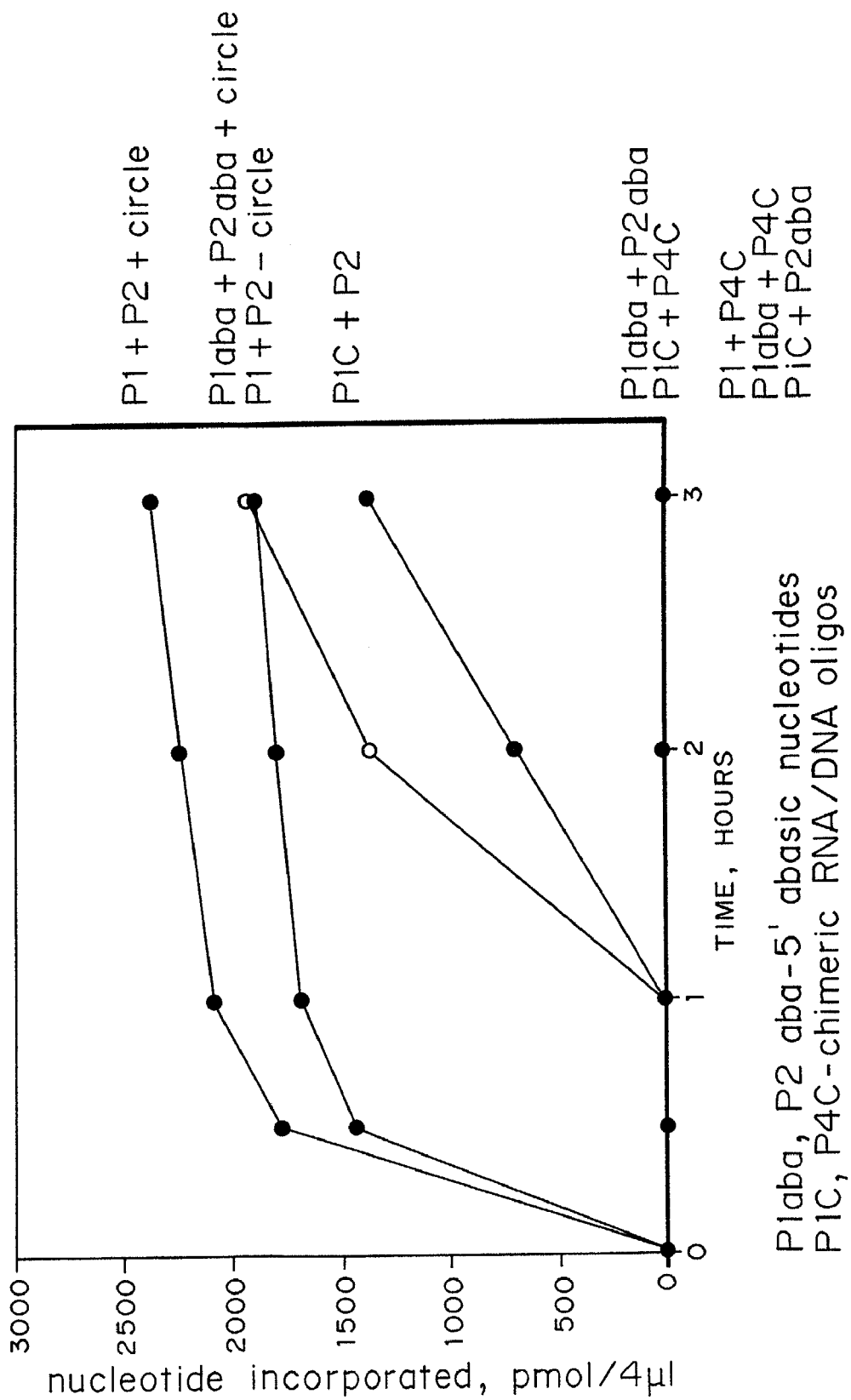

METHOD FOR REDUCING ARTIFACTS IN NUCLEIC ACID AMPLIFICATION

BACKGROUND OF THE INVENTION

The present invention is in the field of nucleic acid amplification, and specifically in the area of reducing amplification artifacts in nucleic acid amplification reactions.

Numerous nucleic acid amplification techniques have been devised, including strand displacement cascade amplification (SDCA)(referred to herein as exponential rolling circle amplification (ERCA)) and rolling circle amplification (RCA)(U.S. Pat. No. 5,854,033; PCT Application No. WO 97/19193; Lizardi et at., *Nature Genetics* 19(3):225–232 (1998)); multiple displacement amplification (MDA)(PCT Application WO 99/18241); strand displacement amplification (SDA)(Walker et al., *Nucleic Acids Research* 20:1691–1696 (1992), Walker et al., *Proc. Natl. Acad. Sci. USA* 89:392–396 (1992)); polymerase chain reaction (PCR) and other exponential amplification techniques involving thermal cycling, self-sustained sequence replication (3SR), nucleic acid sequence based amplification (NASBA), and amplification with Qβ replicase (Birkenmeyer and Mushahwar, *J. Virological Methods* 35:117–126 (1991); Landegren, *Trends Genetics* 9:199–202 (1993)); and various linear amplification techniques involving thermal cycling such as cycle sequencing (Craxton et al., *Methods Companion Methods in Enzymology* 3:20–26 (1991)).

Artifacts—that is, unwanted, unexpected, or non-specific nucleic acid molecules—have been observed in almost all nucleic acid amplification reactions. For example, Stump et al., *Nucleic Acids Research* 27:4642–4648 (1999), describes nucleic acid artifacts resulting from an illegitimate PCR process during cycle sequencing. Stump et al. suggests a way to avoid such artifacts by using certain primers that cannot be fully replicated. Watson, *Amplifications*, 5–6 (1989), and Ferrie et al., *Am. J. Hum. Genet.* 51:251–262 (1992), describe formation of primer-dimer artifacts during PCR. Brownie et al., *Nucleic Acids Research* 25:3235–3241 (1997), suggests a way to avoid primer dimer formation during PCR by adding tails at the 5' end of the PCR primers that results in formation of a non-replicable structure if primer-dimer formation is initiated. Other forms of artifacts can occur in other types of nucleic acid amplification techniques.

Therefore, it is an object of the present invention to provide a method of reducing, preventing, or eliminating artifacts in nucleic acid amplification reactions.

It is another object of the present invention to provide oligonucleotides that, when used in a nucleic acid amplification reaction, can reduce, prevent, or eliminate artifacts in the nucleic acid amplification reaction.

It is another object of the present invention to provide kits for nucleic acid amplification that can reduce, prevent, or eliminate artifacts in the nucleic acid amplification reaction.

BRIEF SUMMARY OF THE INVENTION

Disclosed are compositions and methods useful for reducing the formation of artifacts during nucleic acid amplification reactions. The method uses special oligonucleotides, referred to herein as template-deficient oligonucleotides, that cannot serve as a template for nucleic acid synthesis over part of their length. This prevents the oligonucleotides from serving as effective templates in the formation of artifacts. The disclosed method involves using a template-deficient oligonucleotide as at least one of the oligonucleotides (preferably a primer) in a nucleic acid amplification reaction, where the template-deficient oligonucleotide comprises one or more template-deficient nucleotides, preferably at or near the 5' end of the template-deficient oligonucleotide. The disclosed method is useful for reducing artifacts in any nucleic acid amplification reaction involving oligonucleotides. In a preferred form of the method the nucleic acid amplification reaction does not involve thermal cycling. The disclosed method is effective at reducing non-cycle oligonucleotide-based artifacts. Also disclosed are kits useful for reducing artifacts in nucleic acid amplification reactions. The disclosed kits include a template-deficient oligonucleotide, wherein the template-deficient oligonucleotide comprises one or more template-deficient nucleotides, and a nucleic acid polymerase.

BRIEF DESCRIPTION OF THE DRAWINGS

FIG. 1 is a diagram of the proposed "templating" process leading to formation of artifacts.

FIG. 2 is a diagram of an oligonucleotide with an abasic nucleotide at the 5' end showing that it cannot serve as a template for synthesis of a complete complementary strand.

FIG. 3 is a diagram of an oligonucleotide with two abasic nucleotides at the 5' end showing that it cannot serve as a template for synthesis of a complete complementary strand.

FIG. 4 is a diagram showing how primer dimers could be formed during PCR through non-template (that is, overhanging) addition of an adenosine at the 3' end of the synthesized strand.

FIG. 5 is a diagram of various structures of examples of the disclosed template-deficient oligonucleotides (oligonucleotides 2–15). The region of each oligonucleotide that is template-deficient, template-capable, primer-deficient, and primer-capable is indicated. For comparison, oligonucleotide 1 is a normal oligonucleotide (that is, composed entirely of template- and primer-capable nucleotides).

FIG. 7 is a graph of amount of nucleotide incorporated (in pmol/4 l) versus time (in hours) during exponential rolling circle amplification reactions using various combinations of control primers (P1 and P2) and template-deficient primers (P1aba, P2aba, P1C, and P4C). The P1aba and P2aba primers had two abasic nucleotides at the 5' end. The P1C and P4C primers were chimeric, having 6 deoxyribonucleotides at the 3' end and 18 ribonucleotides at the 5' end. The primers used (and whether a template circle was present) are indicated by annotations to the right of the graph next to the last data point in each curve. The five annotations at the bottom (P1aba+P2aba, P1C+P4C, P1+P4C, P1aba+P4C, and P1C+P2aba) represent reactions having identical curves showing no nucleotide incorporation.

DETAILED DESCRIPTION OF THE INVENTION

Figure 6:
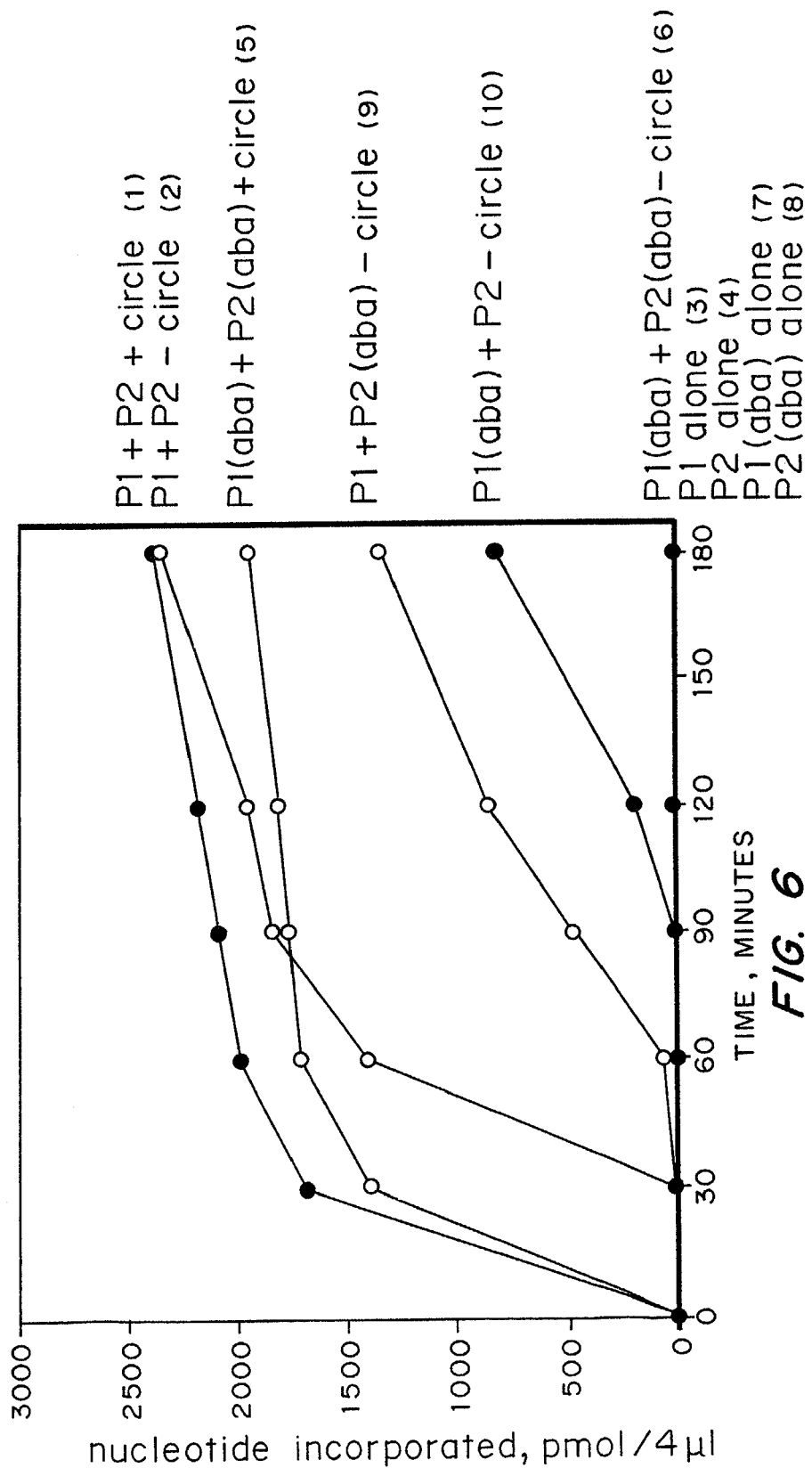
FIG. 6 is a graph of amount of nucleotide incorporated (in pmol/4 l) versus time (in minutes) during exponential rolling circle amplification reactions using various combinations of control primers (P1 and P2) and abasic primers (P1(aba) and P2(aba)). The abasic primers had two abasic nucleotides at the 5' end. The primers used (and whether a template circle was present) are indicated by annotations to the right of the graph next to the last data point in each curve. The five annotations at the bottom (P1(aba)+P2(aba)–circle, P1 alone, P2 alone, P1 (aba) alone, and P2(aba) alone) represent reactions having identical curves showing no nucleotide incorporation. The reaction number, as described in Example 1, represented by each curve is indicated in parentheses next to the annotations.

Nucleic acid amplification techniques using primers are often compromised by the formation of nucleic acid artifacts that are not the product of legitimate amplification. For example, exponential rolling circle amplification (ERCA), an isothermal amplification reaction using two primers complementary to opposite strands of a nucleic acid molecule to be amplified (see strand displacement cascade amplification in PCT Application No. WO 97/19193), sometimes results in formation of oligonucleotide-based artifacts. These artifacts, referred to herein as non-cycle oligonucleotide-based artifacts, are different in structure from primer dimer artifacts that can occur in amplification reactions involving thermal cycling and result from a different mechanism.

For example, artifactual DNA products synthesized by Bst polymerase during ERCA consist of DNA molecules that are long, many kilobase in length, yet occur in the absence of template, or any DNA of like size that could act as a template to yield a product of such a size. The artifact DNA synthesis can occur efficiently in the presence of just two short oligonucleotide primers and Bst alone. The artifactual DNA appears as a collection of products varying greatly in size that appears as a broad smear, or ladder of closely spaced bands, when analyzed by gel electrophoresis.

It has been discovered that non-cycle oligonucleotide-based artifacts could be reduced by using oligonucleotides that could not be replicated to their full length, thereby preventing synthesis of a duplex, blunt-ended structure. Such oligonucleotides are referred to herein as template-deficient oligonucleotides. Such oligonucleotides would be poorly extended out to the ends and would only poorly be able to extend across the nick that is created by the insertion of an interloping oligonucleotide (see FIG. 2).

Disclosed are compositions and methods useful for reducing the formation of primer artifacts during nucleic acid amplification reactions. The method uses special oligonucleotides, referred to herein as template-deficient oligonucleotides, that cannot serve as a template for nucleic acid synthesis over part of their length. This prevents the oligonucleotides from serving as effective templates in the formation of artifacts during a nucleic acid amplification reaction. It is preferred that the template-deficient oligonucleotide be a primer, that all of the primers used in the nucleic acid amplification reaction are template-deficient, and/or that all of the oligonucleotides used in the nucleic acid amplification reaction are template-deficient.

In one form, the disclosed method involves using a template-deficient oligonucleotide where the template-deficient oligonucleotide includes one or more template-deficient nucleotides, where the number and composition of template-capable nucleotides 3' of the template-deficient nucleotide closest to the 3' end of the template-deficient oligonucleotide is sufficient to allow the template-capable nucleotides 3' of the template-deficient nucleotide closest to the 3' end alone to effectively prime nucleic acid synthesis in the nucleic acid amplification reaction. Template-deficient oligonucleotides of this form are referred to herein as 3' open oligonucleotides. Template-deficient oligonucleotides referred to herein as 3' closed oligonucleotides are template-deficient oligonucleotides where the template-deficient oligonucleotide includes one or more template-deficient nucleotides, where the number and composition of template-capable nucleotides 3' of the template-deficient nucleotide closest to the 3' end of the template-deficient oligonucleotide is insufficient to allow the template-capable nucleotides 3' of the template-deficient nucleotide closest to the 3' end alone to effectively prime nucleic acid synthesis in the nucleic acid amplification reaction. Put another way, placing a template-deficient nucleotide at or near the 3' end of an oligonucleotide results in a 3' closed oligonucleotide.

In another form, the disclosed method involves using a template-deficient oligonucleotide where the template-deficient oligonucleotide includes one or more template-deficient nucleotides.

Numerous configurations of template-deficient nucleotides can be used in the disclosed template-deficient oligonucleotides. For example, when the template-deficient oligonucleotide contains one or more template-deficient nucleotides, the template-deficient nucleotides can be at or near the 5' end of the template-deficient oligonucleotide. When the template-deficient oligonucleotide contains two or more template-deficient nucleotides, at least two of the template-deficient nucleotides can be adjacent. In one embodiment, the adjacent template-deficient nucleotides can be within three nucleotides of the 5' end of the template-deficient oligonucleotide. In general, no particular configuration of template-deficient nucleotides is required.

Template-deficient nucleotides are selected from the group consisting of modified nucleotides, derivatized nucleotides, ribonucleotides, and nucleotide analogs. Preferred template-deficient nucleotides are modified nucleotides. Preferred modified nucleotides are abasic nucleotides. Template-deficient nucleotides include abasic nucleotides, nucleotides with an inverted base, fluoro substituted nucleotides, alkyl substituted nucleotides, nucleotides with phenyl substituted ethers, nucleotides with substituted thioethers, nucleotides with phosphate esters, α-nucleotides, 2',3'-dideoxy nucleotides, ribonucleotides, nucleotides derivatized with biotin, nucleotides derivatized with amine, nucleotides derivatized with Hex, nucleotides derivatized with Tet, nucleotides derivatized with Fam, nucleotides derivatized with fluorescein, nucleotides derivatized with rhodamine, nucleotides derivatized with alkaline phosphatase, nucleotides derivatized with horseradish peroxidase, nucleotides derivatized with spacers, nucleotides derivatized with cholesteryl, nucleotides derivatized with DNP-TEG, nucleotides derivatized with psoralen crosslinkers, nucleotides derivatized with intercalating agents, and nucleotides derivatized with PNA conjugates.

Examples of such nucleotides include abasic nucleosides (Beigelman et al., *Bioorganic & Medicinal Chemistry Letters* 4(14):1715–1720 (1994); Moran et al., *Nucleic Acids Res.* 24(11):2044–2052 (1996); Matray and Kool, *Nature* 399:704–708 (1999)), 5'-fluoro substituted nucleosides (Robins and Wnuk, *Tetrahedron Lett.* 29:5729(1988)), 5'-alkyl substituted nucleosides (Ray and Jaxa-Chamiec, *Heterocycles* 31(10): 1777–1780 (1990); Jun-Dong and Li-He, *Synthesis* 909–911 (1990); Tanaka et al., *Tetrahedron Lett.* 30:2567–2570 (1989)), nucleosides with 5'-alkyl or phenyl substituted ethers (Jones et al., *Carbohydrates, Nucleosides, Nucleotides* 4:301 (1977)), 5'-substituted thioethers (Connolly and Rider, *Nucleic Acids Res.* 13:4485 (1985); Connolly, *Nucleic Acids Res.* 15:3131–3139 (1987); Sinha and Cook, *Nucleic Acids Res.* 16:2659 (1988); Kumar et al., *Nucleic Acids Res.* 19:4561 (1991); Zuckermann et al., *Nucleic Acids Res.* 15:5305 (1987); Gupta et al., *Tetrahedron Lett.* 31:2471–2474 (1990); Asseline et al., *Tetrahedron* 48:1233–1254 (1992)), 5'-amines and substituted amines (Connolly and Rider, *Nucleic Acids Res.* 13:4485 (1985); Haralambidis et al., *Nucleic Acids Res.* 15:4857 (1987); Zuckermann et al., *Nucleic Acids Res.* 15:5305 (1987), Li et al., *Nucleic Acids Res.* 15:5275 (1987); Dreyer and Dervan, *Proc. Natl. Acad. Sci. USA* 82:968 (1985)), phosphate esters as 5'-terminators (Tanaka et al., *Tetrahedron Lett.* 30:2567–2570 (1989)), inverted bases or α-nucleosides as 5'-terminators (Bloch et al., *Gene* 72:349 (1988); Sequin, Helv. Chim. Acta. 57:68 (1974)), 2',3'-dideoxy nucleosides as 5'-terminators (Huryn and Okabe, Chem. Rev. 92:1745–1768 (1992)).

The nucleotides or oligonucleotides can also be derivatized with, for example, biotin, dyes such as fluorescein or rhodamine, or proteins such as alkaline phosphatase or horseradish peroxidase. 5'-modifications useful in the disclosed oligonucleotides include 5'-spacers (Durand et al., *Nucleic Acids Res.* 18:6353 (1990); Salunkhe et al., *J. Amer. Chem. Soc.* 114:8768–8772 (1992); Dolinnaya et al., *Nucleic Acids. Res.* 21:5403–5407 (1993); Takeshita et al., *J. Biol. Chem.* 262:10171–10179 (1987); Kalnik et al., *Biochemistry* 27:924–931 (1998)), 5'-biotinylated primers (Cocuzza, *Tetrahedron Lett.* 30:6287–6290 (1989); Nelson et al., *Nucleic Acids Res.* 20:6253–6259 (1992)), 5'-cholesteryl (Mackellar et al., *Nucleic Acids. Res.* 20:3411–3417 (1992); Stein et al., *Biochemistry* 30:2439–2444 (1991)), 5'-DNP-TEG (Will et al, *Carbohydrate Research* 216:315–322 (1991); Grzybowski et al., *Nucleic Acids Res.* 21:1705–1712 (1993)), 5'-psoralen cross-linkers (Pieles and Englisch, *Nucleic Acids Res.* 17:285 (1989); Takasugi et al., *Proc. Natl. Acad. Sci. USA* 88:5602–5606 (1991)), 5'-intercalating agents (Thoung and Chassignol, *Tetrahedron Lett.* 29:5905 (1988)), 5'-PNA conjugates (Nielsen et al., *Science* 254:1497–1500 (1991); Egholm et al., *J. Am. Chem. Soc.* 114:1895–1897 (1992)), 5'-enzyme conjugates (Jablonski et al., *Nucleic Acids. Res.* 14:6115–6128 (1986)), 5'-dye-label (Molecular Probes, Eugene, Oreg.; Research Organics, Cleveland, Ohio).

It is not required that all of the template-deficient nucleotides in a template-deficient oligonucleotide be the same type of nucleotide. For example, a template-deficient oligonucleotide can include both abasic nucleotides and ribonucleotides as template-deficient nucleotides. Such template-deficient nucleotides are template-deficient for different reasons (the abasic nucleotide has no base to serve as a template while the ribonucleotide is not recognized as a template by the polymerase). There are no restrictions on the combinations of different template-deficient nucleotides that can be used in the same template-deficient oligonucleotide. Similarly, it is not required that all template-deficient oligonucleotides used in a nucleic acid amplification reaction have the same types or patterns of template-deficient nucleotides. For example, a primer containing abasic nucleotides can be used with a primer containing inverted nucleotides in the same amplification reaction.

The disclosed template-deficient oligonucleotides can be used with any method of nucleic acid amplification. Preferred forms of nucleic acid amplification for use of the disclosed oligonucleotides include nucleic acid amplification reactions involving exponential amplification, either isothermal or with thermal cycling, nucleic acid amplification reactions requiring exponential amplification, either isothermal or with thermal cycling, nucleic acid amplification reactions involving isothermal linear amplification, nucleic acid amplification reactions requiring isothermal linear amplification, nucleic acid amplification reactions involving rolling circle amplification, nucleic acid amplification reactions involving the polymerase chain reaction, and nucleic acid amplification reactions not involving thermal cycling. Examples of nucleic acid amplification reactions are exponential rolling circle amplification (ERCA) (referred to as strand displacement cascade amplification in PCT Application No. WO 97/19193 and as hyperbranched rolling circle amplification in Lizardi et al., *Nature Genetics* 19(3):225–232 (1998)) and rolling circle amplification (RCA) (U.S. Pat. No. 5,854,033; PCT Application No. WO 97/19193; Lizardi et al., *Nature Genetics* 19(3):225–232 (1998)); multiple displacement amplification (MDA)(PCT Application WO 99/18241); strand displacement amplification (SDA)(Walker et al., *Nucleic Acids Research* 20:1691–1696 (1992), Walker et al., *Proc. Natl. Acad. Sci. USA* 89:392–396 (1992)); nucleic acid sequence based amplification (NASBA) (Compton, *Nature* 350:91–92 (1991)); transcription-mediated amplification (TMA) (Nelson, *Crit Rev Clin Lab Sci* 35:369–414 (1998)); polymerase chain reaction (PCR) and other exponential amplification techniques involving thermal cycling, self-sustained sequence replication (3SR), and amplification with Qβ replicase (Birkenmeyer and Mushahwar, *J. Virological Methods* 35:117–126 (1991); Landegren, *Trends Genetics* 9:199–202 (1993)); various linear amplification techniques involving thermal cycling such as cycle sequencing (Craxton et al., *Methods Companion Methods in Enzymology* 3:20–26 (1991)). The disclosed oligonucleotides and method would be useful in techniques described in Lizardi et al., *Nature Genetics* 3:225–232 (1998), Thomas et al., *Arch Pathol Lab Med* 123:1170–1176 (1999), Baner et al., *Nucleic Acids Research* 26:5073–5078 (1998), and Zhang et al., *Gene* 211:277–285 (1998).

When using 3' closed oligonucleotides as primers, it is preferred that the nucleic acid amplification reaction not involve cycle sequencing, the nucleic acid amplification reaction not require linear amplification via thermal cycling, the nucleic acid amplification reaction not involve linear amplification via thermal cycling, or the nucleic acid amplification reaction involve exponential amplification via thermal cycling.

Also disclosed are kits useful for reducing artifacts in nucleic acid amplification reactions. The disclosed kits include a template-deficient oligonucleotide as described herein and a polymerase. Any form of template-deficient primer as disclosed herein can be included in the disclosed kits.

While not wishing to be limited to any particular mechanism, it is believed that non-cycle oligonucleotide-based artifacts could be generated in the following manner. First, mispriming occurs such that, for example, one oligonucleotide partially anneals to a second oligonucleotide and is extended to the end of the oligonucleotide (see FIG. 1). This blunt-ended product may sit in the polymerase active site for an extended period of time. The enzyme binding site for the single-stranded template DNA strand is vacant, and then a second oligonucleotide transiently slips into the active site. Such binding may be stabilized by interaction with the amino acids in the enzyme single-stranded template binding site or the stacking energy between the 5' template-strand base and the 3' end interloping-strand base. Such binding would ordinarily not be very stable or long-lived but may be long enough for a nucleotide to be added to the 3' end of the nascent strand. This would further stabilize the interloping oligonucleotide which could then be copied quickly to its full extent. As a result, the enzyme sits with a blunt-ended duplex in its active site, and another oligonucleotide can then fit into the template-strand binding site and the cycle repeats itself. In this way, long DNA products may be generated. This process of artifactual synthesis of long products by the binding of successive oligonucleotides into the template-strand binding site is referred to herein as templating (see FIG. 1).

Definitions

A template-deficient oligonucleotide is an oligonucleotide with at least one region that cannot serve as a template for nucleic acid synthesis. The functional effect is that a template-deficient oligonucleotide cannot be fully replicated. A template-deficient oligonucleotide can be made by, for example, including template-deficient nucleotides in the oligonucleotide. Whether an oligonucleotide is a template-deficient oligonucleotide can depend on the nucleic acid polymerase being used since certain types of nucleotides can be used as a template by some polymerases but not others. For example, many DNA polymerases require a DNA template. Accordingly, as used herein, whether an oligonucleotide is template-deficient is determined based on the nucleic acid polymerase being used in the nucleic acid amplification reaction. Primers that are template-deficient oligonucleotides are referred to herein as template-deficient primers.

Template-deficient nucleotides are nucleotides or nucleotide analogs that (when contained in a nucleic acid molecule) cannot serve as a template for nucleic acid synthesis. Examples of template-deficient nucleotides include abasic nucleotides and derivatized nucleotides. The functional effect is that a template-deficient nucleotide prevents synthesis of a nucleic acid strand complementary to a nucleic acid strand containing a template-deficient nucleotide at or beyond the site of the template-deficient nucleotide. Template-capable nucleotides are nucleotides that are not template-deficient. Whether a nucleotide is a template-deficient nucleotide can depend on the nucleic acid polymerase being used since certain types of nucleotides can be used as a template by some polymerases but not others. For example, many DNA polymerases require a deoxyribonucleotide template. Accordingly, as used herein, whether a nucleotide is template-deficient is determined based on the nucleic acid polymerase being used in the nucleic acid amplification reaction.

Oligonucleotide-based artifacts are nucleic acids that are formed in a nucleic acid amplification reaction in the absence of nucleic acids other than the oligonucleotides. Oligonucleotide-based artifacts are to be distinguished from artifacts that result from unintended or illegitimate priming of a template nucleic acid (most often a template that is not the intended template). It should be noted that oligonucleotide-based artifacts may occur in the presence of nucleic acids other than the oligonucleotides. The formation of oligonucleotide-based artifacts in the absence of other nucleic acids is used primarily to distinguish oligonucleotide-based artifacts from other types of nucleic acid amplification artifacts. Non-cycle oligonucleotide-based artifacts are oligonucleotide-based artifacts that are formed in nucleic acid amplification reactions not involving thermal cycling. Cycle oligonucleotide-based artifacts are oligonucleotide-based artifacts that are formed in nucleic acid amplification reactions that involve thermal cycling where formation of the artifacts depends on thermal cycling. Primer-based artifacts are oligonucleotide-based artifacts that are formed from or by primers.

Primer-deficient nucleotides are nucleotides or nucleotide analogs that (when contained in a nucleic acid molecule) cannot hybridize (i.e. cannot hydrogen bond) to a complementary nucleotide. Examples of primer-deficient nucleotides include abasic nucleotides and derivatized nucleotides. The functional effect is that a primer-deficient nucleotide prevents formation of a hybrid to a nucleic acid strand containing a primer-deficient nucleotide at the site of the primer-deficient nucleotide. Primer-capable nucleotides are nucleotides that are not primer-deficient. Examples of primer-capable nucleotides are common ribonucleotides and deoxyribonucleotides.

A 3' open oligonucleotide is a template-deficient oligonucleotide where the template-deficient oligonucleotide includes one or more template-deficient nucleotides, and where the number and composition of template-capable nucleotides 3' of the template-deficient nucleotide closest to the 3' end of the template-deficient oligonucleotide is sufficient to allow the template-capable nucleotides 3' of the template-deficient nucleotide closest to the 3' end alone to effectively prime nucleic acid synthesis in the nucleic acid amplification reaction. A 3' closed oligonucleotide is a template-deficient oligonucleotide where the template-deficient oligonucleotide includes one or more template-deficient nucleotides, where the number and composition of template-capable nucleotides 3' of the template-deficient nucleotide closest to the 3' end of the template-deficient oligonucleotide is insufficient to allow the template-capable nucleotides 3' of the template-deficient nucleotide closest to the 3' end alone to effectively prime nucleic acid synthesis in the nucleic acid amplification reaction. Put another way, placing a template-deficient nucleotide at or near the 3' end of an oligonucleotide results in a 3' closed oligonucleotide, while keeping the region of the oligonucleotide at or near the 3' end free of template-deficient nucleotides results in a 3' open oligonucleotide.

As used herein, a nucleic acid amplification reaction is said to "require" a specified component or condition when the amplification reaction would not function or would not result in the desired amplification. For example, PCR requires thermal cycling since PCR amplification depends on separation of synthesized strands and annealing of primers to both template and synthesized strands for another round of replication. As used herein, a nucleic acid amplification reaction is said to "involve" a specified component or condition when the amplification reaction uses the component or condition. Whether a given amplification reaction involves a particular component depends on the specific reaction involved. For example, a PCR reaction may be performed using labeled primers. Such a reaction can thus be said to "involve" labeled primers. However, since PCR can function without such primers, they would not be considered "required" for PCR. All amplification reactions that "require" a given component or condition also "involve" that component or condition, but not all amplification reactions that "involve" a given component or condition also "require" that component or condition.

Linear amplification refers to nucleic acid amplification that produces, or is designed to produce, an increase in the target nucleic acid directly proportional to the amount of target nucleic acid in the reaction. For example, cycle sequencing produces one strand (or, more precisely, one chain-terminated partial strand) for every target strand present. The amplification is linear since the synthesized strands are not used as templates in subsequent rounds. Exponential amplification refers to nucleic acid amplification that produces, or is designed to produce, an increase in the target nucleic acid geometrically proportional to the amount of target nucleic acid in the reaction. For example, PCR produces one strand for every original target strand and for every synthesized strand present. The amplification is exponential since the synthesized strands are used as templates in subsequent rounds. An amplification reaction need not actually produce exponentially increasing amounts of nucleic acid to be considered exponential amplification, so long as the amplification reaction is designed to produce such increases.

Cycle sequencing refers to nucleic acid sequencing reactions that require thermal cycling. Cycling, in a nucleic acid amplification reaction, refers to a periodic, repeating change in some condition of the reaction. Minor changes in the condition, such as a slight variation in temperature due to temperature-holding limits of a water bath, is not considered to be cycling, especially where such variations do not have a functional effect on the reaction. Thermal cycling, in a nucleic acid amplification reaction, refers to a periodic, repeating change in the temperature of the reaction of the reaction. PCR requires thermal cycling.

A nucleic acid amplification reaction is a reaction that results in synthesis of more than one copy of all or part of one or more nucleic acid molecules. As used herein, a nucleic acid amplification reaction includes assays, reactions, techniques, and procedures that involve nucleic acid amplification. The fact that such assays, reactions, techniques, and procedures have a goal other than or in addition to nucleic acid amplification—such as nucleic acid sequencing or nucleic acid detection—does not prevent it from being a nucleic acid amplification reaction.

As used herein, nucleoside refers to adenosine, guanosine, cytidine, uridine, 2'-deoxyadenosine, 2'-deoxyguanosine, 2'-deoxycytidine, or thymidine. A nucleoside analog is a chemically modified form of nucleoside containing a chemical modification at any position on the base or sugar portion of the nucleoside. As used herein, the term nucleoside analog encompasses, for example, both nucleoside analogs based on naturally occurring modified nucleosides, such as inosine and pseudouridine, and nucleoside analogs having other modifications, such as modifications to the 2' position of the sugar. As used herein, nucleotide refers to a phosphate derivative of nucleosides as described above, and a nucleotide analog is a phosphate derivative of nucleoside analogs as described above. The subunits of oligonucleotide analogs, such as peptide nucleic acids, are also considered to be nucleotide analogs.

As used herein, a ribonucleotide is a nucleotide having a 2' hydroxyl function. Analogously, a 2'-deoxyribonucleotide is a nucleotide having only 2' hydrogens. Thus, ribonucleotides and deoxyribonucleotides as used herein refer to naturally occurring nucleotides having nucleoside components adenosine, guanosine, cytidine, and uridine, or 2'-deoxyadenosine, 2'-deoxyguanosine, 2'-deoxycytidine, and thymidine, respectively, without any chemical modification. Ribonucleosides, deoxyribonucleosides, ribonucleoside analogs and deoxyribonucleoside analogs are similarly defined except that they lack the phosphate group, or an analog of the phosphate group, found in nucleotides and nucleotide analogs.

As used herein, oligonucleotide analogs are polymers of nucleic acid-like material with nucleic acid-like properties, such as sequence dependent hybridization, that contain at one or more positions, a modification away from a standard RNA or DNA nucleotide. A preferred example of an oligonucleotide analog is peptide nucleic acid.

The meaning of the above terms is further illustrated by usage of the terms elsewhere herein. The meaning of additional terms used herein but not defined above can generally be understood by common usage in the art and by the context of their usage. The above definitions are not intended to be an exclusive list of terms used and defined herein.

Oligonucleotides

A variety of oligonucleotide structures can be used to create template-deficient oligonucleotides. In general, template-deficient nucleotides useful for making template-deficient oligonucleotides include modified nucleotides, derivatized nucleotides, ribonucleotides, and nucleotide analogs.

For example, the oligonucleotide can have one or more abasic nucleotides, one or more nucleotides with an inverted base, fluoro substituted nucleosides, one or more alkyl substituted nucleosides, one or more nucleosides with alkyl groups, one or more nucleoside with phenyl substituted ethers, one or more nucleotides with substituted thioethers, one or more nucleosides with phosphate esters, one or more α-nucleosides, one or more 2',3'-dideoxy nucleosides, or one or more nucleotides derivatized with compounds such as biotin, amine, Hex, Tet, Fam, fluorescein, rhodamine, alkaline phosphatase, horseradish peroxidase, spacers, cholesteryl, DNP-TEG, psoralen cross-linkers, intercalating agents, PNA conjugates, other enzyme conjugates, and other dye-labels.

One class of modified or derivatized nucleotides have the structure:

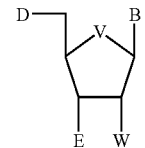

Each B can be —H, —OH, —COOH, —CONH$_2$, —CONHR$^1$, —CONR$^1$R$^2$, NH$_2$, —NHR$^1$, —NR$^1$R$^2$, —NHCOR$^1$, —SH, SR$^1$, —F, —ONH$_2$, —ONHR$^1$, —ONR$^1$R$^2$, —NHOH, —NHOR$^1$, —NR$^2$OH, —NR$^2$OR$^1$, substituted or unsubstituted C$_1$–C$_{10}$ straight chain or branched alkyl, substituted or unsubstituted C$_2$–C$_{10}$ straight chain or branched alkenyl, substituted or unsubstituted C$_2$–C$_{10}$ straight chain or branched alkynyl, substituted or unsubstituted C$_1$–C$_{10}$ straight chain or branched alkoxy, substituted or unsubstituted C$_2$–C$_{10}$ straight chain or branched alkenyloxy, and substituted or unsubstituted C$_2$–C$_{10}$ straight chain or branched alkynyloxy. The substituents for W groups are independently halogen, cyano, amino, carboxy, ester, ether, carboxamide, hydroxy, or mercapto. R$^1$ and R$^2$ can be substituted or unsubstituted alkyl, alkenyl, or alkynyl groups, where the substituents are independently halogen, cyano, amino, carboxy, ester, ether, carboxamide, hydroxy, or mercapto.

Each V can be an O, S, NH, or CH$_2$ group.

Each W can be —H, —OH, —COOH, —CONH$_2$, —CONHR$^1$, —CONR$^1$R$^2$, —NH$_2$, —NHR$^1$, —NR$^1$R$^2$, —NHCOR$^1$, —SH, SR$^1$, —F, —ONH$_2$, —ONHR$^1$, —ONR$^1$R$^2$, —NHOH, —NHOR$^1$, —NR$^2$OH, —NR$^2$OR$^1$, substituted or unsubstituted C$_1$–C$_{10}$ straight chain or branched alkyl, substituted or unsubstituted C$_2$–C$_{10}$ straight chain or branched alkenyl, substituted or unsubstituted C$_2$–C$_{10}$ straight chain or branched alkynyl, substituted or unsubstituted C$_1$–C$_{10}$ straight chain or branched alkoxy, substituted or unsubstituted C$_2$–C$_{10}$ straight chain or branched alkenyloxy, and substituted or unsubstituted C$_2$–C$_{10}$ straight chain or branched alkynyloxy. The substituents for W groups are independently halogen, cyano, amino, carboxy, ester, ether, carboxamide, hydroxy, or mercapto. R$^1$ and R$^2$ can be substituted or unsubstituted alkyl, alkenyl, or alkynyl groups, where the substituents are independently halogen, cyano, amino, carboxy, ester, ether, carboxamide, hydroxy, or mercapto.

D and E are residues which together form a phosphodiester or phosphorothioate diester bond between adjacent nucleosides or nucleoside analogues or together form an analogue of an internucleosidic bond.

All of the above modifications may make it difficult for a polymerase to add nucleotides opposite such modified nucleotides or extend synthesis beyond such modified nucleotides. A combination of nucleotides having different modifications, derivatizations, or substitutions can be used in a single template-deficient oligonucleotide. Similarly, primers having different types of modifications, derivatizations, or substitutions can be used in the same amplification reaction (see Example 2 and FIG. 7).

Template-deficient oligonucleotides can also be made without using modified nucleotides, derivatized nucleotides, or nucleotide analogs. For example, ordinary ribonucleotides can be used as template-deficient nucleotides, depending on the polymerase used. Polymerases that require a DNA template will not be able to use ribonucleotides in the primer.

It is preferred that template-deficient oligonucleotides have at least two consecutive or adjacent template-deficient nucleotides. Such an arrangement reduces the chance that synthesis could pass over a template-deficient region in the oligonucleotide. For example, some polymerases, such as Taq DNA polymerase, add an overhanging 3' nucleotide to a blunt-ended double-stranded DNA structure. This might overhang the 5' abasic base in the templating scenario and allow templating to occur anyway. Use of two consecutive abasic nucleotides should inhibit synthesis across the nick (see FIG. 3). The examples shows the reduction in artifacts in an ERCA reaction when two primer oligonucleotides, P1 and P2, each with two 5' abasic nucleotides are used (see FIG. 6).

A subset of the disclosed oligonucleotides are preferred for use in amplification reactions involving thermal cycling, such as PCR. Unlike the primers of Stump et al.—which have few enough template-capable nucleotides 3' of the most 3' template-deficient nucleotide to prevent synthesis of a strand to which the primer can effectively prime—the subset of the disclosed primers preferred for thermal cycling reactions will have enough template-capable nucleotides 3' of the most 3' template-deficient nucleotide to allow effective priming of synthesized strands.

Template-deficient nucleotides can be placed anywhere in an oligonucleotide. It may be desirable to keep the 5' end of an oligonucleotide free of template-deficient nucleotides. For example, oligonucleotides with 5' abasic residues or other modifications may not be effectively labeled by phosphorylation using T4 polynucleotide kinase and $\gamma^-$P-ATP.

Method

The disclosed method involves using one or more of the disclosed template-deficient oligonucleotides in a nucleic acid amplification reaction of interest. Most commonly, the disclosed oligonucleotides will be used as primers in the amplification reaction of interest. Where more than one oligonucleotide is needed or used in the reaction, it is preferred that all of the oligonucleotides in the reaction be template-deficient primers. As used herein, a nucleic acid amplification reaction includes assays, reactions, techniques, and procedures that involve nucleic acid amplification.

The advantage of a nucleic acid amplification reaction that is not susceptible artifacts is that the nucleic acid synthesis products will be specific for the input or target template. In particular, false positives in detection assays involving nucleic acid amplification—caused by artifactual nucleic acid synthesis not dependent on the presence of the target sequence—will be reduced. A preferred nucleic acid amplification reaction for use with the disclosed method if exponential rolling circle amplification (ERCA). The advantage of an ERCA reaction that is not susceptible to primer artifacts is that the DNA synthesis products will be specific for the input template and the yield of DNA synthesis products will be in direct proportion to the quantity of input template.

The disclosed method differs from the method described in Stump et al., *Nucleic Acids Research* 27:4642–4648 (1999). In Stump et al., the artifact resulted from the thermal cycling in a PCR reaction. This PCR artifact resulted because the product of one round of replication was a template for subsequent rounds. Such artifacts are referred to herein as cycle oligonucleotide artifacts. Stump et al. eliminated the cycle oligonucleotide artifact by using primers that could not be fully replicated such that the synthesized strand did not contain enough sequence complementary to the primer to allow the primer to prime synthesis on the synthesized strand (these primers are 3' closed oligonucleotides as defined herein). In contrast, 3' open oligonucleotides as defined herein do allow synthesis of a strand that contains enough sequence complementary to the primer to allow the primer to prime synthesis on the synthesized strand. Further, such primers do not yield a blunt, duplex DNA end such as is required for the templating artifact (that is, a non-cycle oligonucleotide artifact) to occur during the isothermal amplification reactions.

The disclosed method is an improvement of nucleic acid amplification reactions making them more specific. In particular, the disclosed method improves the results when ERCA is used for all applications that ERCA may be used for, such as in vitro diagnostics and SNP analysis in a multi-well format. The disclosed method may also yield an improvement of PCR and other amplification methods involving thermal cycling, and can be used with any PCR or other thermal cycling technique. For use in PCR and other amplification reactions involving thermal cycling, it is preferred that the primer be a 3' open oligonucleotide (that is, an oligonucleotide that includes a sufficient number of template-capable nucleotides at the 3' end of the primer to allow synthesis of a complement to a sufficient portion of the primer to allow efficient priming by the primer under the amplification conditions used).

EXAMPLES

Example 1

Elimination of Primer Artifacts in Exponential Rolling Circle Amplification Using Primers With Abasic Nucleotides This example demonstrates that significant primer artifacts are generated in ERCA when no template is present, and that template-deficient primers having two abasic nucleotides at the 5' end eliminate these primer artifacts. As with most nucleic acid amplification techniques used to detect specific nucleic acids, artifactual production of spurious nucleic acids in the absence of the nucleic acid to be detected can result in false positive assays. In assays where the nucleic acid to be detected is present, artifactual production of spurious nucleic acids can affect the accuracy of the assay both qualitatively and, most significantly, quantitatively. This example demonstrates the elimination of such artifacts.

Ten reactions were carried out under the conditions used for ERCA in order to illustrate the reduction of primer-based artifacts by using primers containing two template-deficient nucleotides at the 5' ends. Reactions (30 µl) contained 20 mM Tris-HCl, 10 mM KCl, 10 mM $(NH_4)_2SO_4$, 2 mM MgSO4, 0.1% TRITON X-100 (pH 8.8 at 25° C.) (TRITON is a registered trademark of Union Carbide Chemicals and Plastics Co., Inc., Danbury, Conn.). In addition, reactions contained 400 μM deoxyribonucleoside triphosphates, α-[$^{32}$P] dCTP, specific activity 169 cpm/pmol total dNTP, and 8 units Bst DNA polymerase. ERCA primers were added as indicated, where 'aba' indicates the presence of an abasic nucleotide residue.

P1 (5' end template-capable)
5' CTA AAG CTG AGA CAT GAC GAG TC 3' (SEQ ID NO:1)
P2 (5' end template-capable)
5' GTG ATT CCA CCT TCT CC 3' (SEQ ID NO:2)
P1aba (5' end template-deficient)
5' (aba)(aba) CTA AAG CTG AGA CAT GAC GAG TC 3' (SEQ ID NO:3)
P2aba (5' end template-deficient)
5' (aba)(aba) GTG ATT CCA CCT TCT CC 3' (SEQ ID NO:4)

Reactions contained single-stranded circular ERCA template DNA designated 'G542X gap padlock circle' as indicated, prepared as described by Lizardi et al., *Nature Genetics* 3:225–232 (1998).

| Reaction | Additions |
| --- | --- |
| 1 | P1 + P2 + G542X gap padlock circle |
| 2 | P1 + P2 |
| 3 | P1 |
| 4 | P2 |
| 5 | P1aba + P2aba + G542X gap padlock circle |
| 6 | P1aba + P2aba |
| 7 | P1aba |
| 8 | P2aba |
| 9 | P1 + P2aba |
| 10 | P1aba + P2 |

Reactions were assembled on ice and incubated for 30 minutes on ice. Reactions were initiated by placing them at 65° C. and incubated further for 3 hours at 65° C. Aliquots (4 μl) were taken at 0.5, 1, 1.5, 2, and 3 hours and spotted onto DE81 filter paper in order to quantitate DNA synthesis by the incorporation of radioactive deoxyribonucleotide. The results are shown in FIG. 6.

As can be seen, significant artifactual DNA production occurs in the absence of template when using template-capable primers (see P1+P2–circle curve). Such artifactual DNA is eliminated when template-deficient primers are used (see P1(aba)+P2(aba)–circle curve). The use of template-deficient primers does not prevent legitimate amplification (see P1(aba)+P2(aba)+circle curve). Use of one template-deficient primer and one template-capable primer still results in artifacts, but at a reduced level (see P1+P2(aba)–circle and P1(aba)+P2–circle curves).

Example 2

Elimination of Primer Artifacts in Exponential Rolling Circle Amplification Using Primers With Abasic Nucleotides, Ribonucleotides This example demonstrates that that template-deficient primers having different types of template-deficient nucleotides, used either alone or in combination, can eliminate primer artifacts of ERCA.

Nine reactions were carried out under the conditions described in Example 1. ERCA primers were added as indicated. P1C and P4C are chimeric RNA/DNA oligonucleotides, having 2'-O-methyl ribonucleotides at the 5' end, as indicated by the use of lower case letters in the sequence. There are 20 2'-O-methyl ribonucleotides at the 5' end of P1C and 18 2'-O-methyl ribonucleotides at the 5' end of P4C. The six nucleotides at the 3' end of P1C and P4C are deoxyribonucleotides, as indicated by the use of capital letters in the sequence.

P1C (5' end template-deficient)
5' aaactaaagctgagacatga CGAGTC 3' (SEQ ID NO:5)
P4C (5' end template-deficient)
5' agtttaatacgactcact ATAGGG 3' (SEQ ID NO:6)

| Reaction | Additions |
| --- | --- |
| 1 | P1 + P2 + G542X gap padlock circle |
| 2 | P1 + P2 |
| 3 | P1aba + P2aba + G542X gap padlock circle |
| 4 | P1aba + P2aba |
| 5 | P1C + P4C |
| 6 | P1 + P4C |
| 7 | P1C + P2 |
| 8 | P1aba + P4C |
| 9 | P1C + P2aba |

Reactions were assembled on ice and incubated for 30 minutes on ice. Reactions were initiated by placing them at 65° C. and incubated further for 3 hours at 65° C. Aliquots (4 l) were taken at 0.5, 1, 2, and 3 hours and spotted onto DE81 filter paper in order to quantitate DNA synthesis by the incorporation of radioactive deoxyribonucleotide. These primers were used both in matched pairs (normal with normal, abasic with abasic, chimeric with chimeric) and in mismatched pairs (abasic with chimeric, abasic with normal, chimeric with normal). The results are shown in FIG. 7.

As can be seen, all combinations of template-deficient primers prevent artifact formation (see P1aba+P2aba, P1C+P4C, P1aba+P4C and P1C+P2aba curves). This includes combinations of template-deficient primers having different types of template-deficient nucleotides (see P1 aba+P4C and P1C+P2aba curves). Use of one template-deficient primer and one template-capable primer can still results in artifacts (see P1C+P2 curve), but not always (see P1+P4C curve).

The results are summarized in the following table.

| Primer Pair | Non-specific DNA Synthesis |
| --- | --- |
| P1 + P2 | yes |
| P1aba + P2aba | no |
| P1C + P4C | no |
| P1 + P4C | no |
| P1C + P2 | yes (reduced) |
| P1aba + P4C | no |
| P1C + P2aba | no |

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to "the antibody" is a reference to one or more antibodies and equivalents thereof known to those skilled in the art, and so forth.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described. Publications cited herein and the material for which they are cited are specifically incorporated by reference. Nothing herein is to be construed as an admission that the invention is not entitled to antedate such disclosure by virtue of prior invention.

Those skilled in the art will recognize, or be able to ascertain using no more than routine experimentation, many equivalents to the specific embodiments of the invention described herein. Such equivalents are intended to be encompassed by the following claims.

We claim:

1. A method of reducing formation of artifacts in a nucleic acid amplification reaction, the method comprising
   conducting a nucleic acid amplification reaction using a template-deficient oligonucleotide as a primer and using a polymerase,
   wherein the template-deficient oligonucleotide comprises one or more template-deficient nucleotides,
   wherein the number and composition of template-capable nucleotides 3' of the template-deficient nucleotide closest to the 3' end of the template-deficient oligonucleotide is sufficient to allow the template-capable nucleotides 3' of the template-deficient nucleotide closest to the 3' end alone to effectively prime nucleic acid synthesis in the nucleic acid amplification reaction reaction,
   wherein the template-deficient oligonucleotide is template-deficient when used in a nucleic acid amplification reaction with the polymerase.

2. The method of claim 1 wherein the one or more template-deficient nucleotides are at the 5' end of the template-deficient oligonucleotide.

3. The method of claim 1 wherein the template-deficient oligonucleotide comprises two or more template-deficient nucleotides, wherein at least two of the two or more template-deficient nucleotides are adjacent.

4. The method of claim 3 wherein the two or more adjacent template-deficient nucleotides are within three nucleotides of the 5' end of the template-deficient oligonucleotide.

5. The method of claim 1 wherein the template-deficient nucleotides are selected from the group consisting of modified nucleotides, derivatized nucleotides, ribonucleotides, and nucleotide analogs.

6. The method of claim 1 wherein the template-deficient oligonucleotide comprises two or more template-deficient nucleotides, wherein at least two of the two or more template-deficient nucleotides are different.

7. The method of claim 1 wherein the template-deficient oligonucleotide comprises two or more template-deficient nucleotides, wherein at least two of the two or more template-deficient nucleotides are template-deficient for different reasons.

8. The method of claim 5 wherein the template-deficient nucleotides are modified nucleotides.

9. The method of claim 5 wherein the modified nucleotides are abasic nucleotides.

10. The method of claim 5 wherein the template-deficient nucleotides are selected from the group consisting of abasic nucleotides, nucleotides with an inverted base, fluoro substituted nucleotides, alkyl substituted nucleotides, nucleotides with phenyl substituted ethers, nucleotides with substituted thioethers, nucleotides with phosphate esters, α-nucleotides, 2',3'-dideoxy nucleotides, ribonucleotides, nucleotides derivatized with biotin, nucleotides derivatized with amine, nucleotides derivatized with Hex, nucleotides derivatized with Tet, nucleotides derivatized with Fam, nucleotides derivatized with fluorescein, nucleotides derivatized with rhodamine, nucleotides derivatized with alkaline phosphatase, nucleotides derivatized with horseradish peroxidase, nucleotides derivatized with spacers, nucleotides derivatized with cholesteryl, nucleotides derivatized with DNP-TEG, nucleotides derivatized with psoralen crosslinkers, nucleotides derivatized with intercalating agents, and nucleotides derivatized with PNA conjugates.

11. The method of claim 1 wherein the nucleic acid amplification reaction does not involve cycle sequencing.

12. The method of claim 11 wherein the nucleic acid amplification reaction does not require linear amplification via thermal cycling.

13. The method of claim 12 wherein the nucleic acid amplification reaction does not involve linear amplification via thermal cycling.

14. The method of claim 1 wherein the nucleic acid amplification reaction involves exponential amplification via thermal cycling.

15. The method of claim 14 wherein the nucleic acid amplification reaction requires exponential amplification via thermal cycling.

16. The method of 14 wherein the nucleic acid amplification reaction involves the polymerase chain reaction.

17. The method of claim 1 wherein the nucleic acid amplification does not involve thermal cycling.

18. The method of 17 wherein the nucleic acid amplification is rolling circle amplification.

19. The method of claim 1 wherein the nucleic acid amplification reaction is selected from the group consisting of exponential rolling circle amplification (ERCA), rolling circle amplification (RCA), multiple displacement amplification (MDA), strand displacement amplification (SDA), nucleic acid sequence based amplification (NASBA), transcription-mediated amplification (TMA), polymerase chain reaction (PCR), self-sustained sequence replication (3SR), amplification with Q replicase, and cycle sequencing.

20. The method of claim 1 wherein all of the primers used in the nucleic acid amplification reaction are template-deficient.

21. The method of claim 1 wherein all of the oligonucleotides used in the nucleic acid amplification reaction are template-deficient.

22. A method of reducing formation of artifacts in a nucleic acid amplification reaction, the method comprising
   conducting a nucleic acid amplification reaction using a template-deficient oligonucleotide as a primer and using a polymerase,
   wherein the template-deficient oligonucleotide comprises one or more template-deficient nucleotides, wherein the one or more adjacent template-deficient nucleotides are within three nucleotides of the 5' end of the template-deficient oligonucleotide,
   wherein the number and composition of template-capable nucleotides 3' of the template-deficient nucleotide closest to the 3' end of the template-deficient oligonucleotide is sufficient to allow the template-capable nucleotides 3' of the template-deficient nucleotide closest to the 3' end alone to effectively prime nucleic acid synthesis in the nucleic acid amplification reaction, wherein the template-deficient oligonucleotide is template-deficient when used in a nucleic acid amplification reaction with the polymerase.

23. The method of claim 22, wherein the modified nucleotides are abasic nucleotides.

24. A method of reducing formation of artifacts in a nucleic acid amplification reaction, the method comprising conducting a nucleic acid amplification reaction using a template-deficient oligonucleotide as a primer and using a polymerase, wherein the template-deficient oligonucleotide comprises one or more template-deficient nucleotides, wherein the modified nucleotides are abasic nucleotides, wherein the number and composition of template-capable nucleotides 3' of the template-deficient nucleotide closest to the 3' end of the template-deficient oligonucleotide is sufficient to allow the template-capable nucleotides 3' of the template-deficient nucleotide closest to the 3' end alone to effectively prime nucleic acid synthesis in the nucleic acid amplification reaction, wherein the template-deficient oligonucleotide is template-deficient when used in a nucleic acid amplification reaction with the polymerase.

25. A method of reducing formation of artifacts in a nucleic acid amplification reaction, the method comprising conducting a nucleic acid amplification reaction using a template-deficient oligonucleotide as a primer and using a polymerase, wherein the template-deficient oligonucleotide comprises one or more template-deficient nucleotides, wherein the one or more adjacent template-deficient nucleotides are within three nucleotides of the 5' end of the template-deficient oligonucleotide, wherein the modified nucleotides are abasic nucleotides, wherein the number and composition of template-capable nucleotides 3' of the template-deficient nucleotide closest to the 3' end of the template-deficient oligonucleotide is sufficient to allow the template-capable nucleotides 3' of the template-deficient nucleotide closest to the 3' end alone to effectively prime nucleic acid synthesis in the nucleic acid amplification reaction, wherein the template-deficient oligonucleotide is template-deficient when used in a nucleic acid amplification reaction with the polymerase.

* * * * *